United States Patent
Bugrim et al.

(10) Patent No.: US 7,660,709 B2
(45) Date of Patent: Feb. 9, 2010

(54) BIOINFORMATICS RESEARCH AND ANALYSIS SYSTEM AND METHODS ASSOCIATED THEREWITH

(75) Inventors: Andrej Bugrim, St. Joseph, MI (US); Craig P. Webb, Rockford, MI (US)

(73) Assignee: Van Andel Research Institute, Grand Rapids, MI (US)

( * ) Notice: Subject to any disclaimer, the term of this patent is extended or adjusted under 35 U.S.C. 154(b) by 190 days.

(21) Appl. No.: 11/945,692

(22) Filed: Nov. 27, 2007

(65) Prior Publication Data

US 2009/0138251 A1 May 28, 2009

Related U.S. Application Data

(63) Continuation-in-part of application No. 11/186,091, filed on Jul. 21, 2005, now abandoned, which is a continuation of application No. 11/084,290, filed on Mar. 18, 2005, now abandoned.

(60) Provisional application No. 60/554,295, filed on Mar. 18, 2004.

(51) Int. Cl.
 *G06F 17/10* (2006.01)
(52) U.S. Cl. ............... 703/2; 702/19; 702/181; 703/11; 706/45; 707/3; 707/104.1
(58) Field of Classification Search ........ None
 See application file for complete search history.

(56) References Cited

U.S. PATENT DOCUMENTS

| | | | |
|---|---|---|---|
| 5,811,235 A | 9/1998 | Jeffreys | |
| 5,853,989 A | 12/1998 | Jeffreys et al. | |
| 5,853,995 A | 12/1998 | Lee | |
| 6,109,776 A | 8/2000 | Haas | |
| 6,203,987 B1 | 3/2001 | Friend et al. | |
| 6,300,078 B1 | 10/2001 | Friend et al. | |
| 6,308,170 B1 | 10/2001 | Balaban | |
| 6,349,265 B1 | 2/2002 | Pitman et al. | |
| 6,405,195 B1 | 6/2002 | Ahlberg | |
| 6,408,321 B1 | 6/2002 | Platt | |
| 6,453,241 B1 | 9/2002 | Bassett, Jr. et al. | |
| 6,468,476 B1 | 10/2002 | Friend et al. | |
| 6,607,887 B2 | 8/2003 | Chee | |
| 2002/0042681 A1 | 4/2002 | Califano et al. | |
| 2002/0165674 A1 | 11/2002 | Bassett, Jr. et al. | |
| 2003/0033127 A1 | 2/2003 | Lett | |
| 2003/0065535 A1 | 4/2003 | Karlov et al. | |
| 2003/0093226 A1 | 5/2003 | Ashby et al. | |
| 2003/0093227 A1 | 5/2003 | Stoughton et al. | |
| 2003/0120642 A1 | 6/2003 | Egilsson et al. | |
| 2003/0129660 A1* | 7/2003 | Zien et al. ............ | 435/7.1 |
| 2003/0146942 A1 | 8/2003 | Helgason et al. | |
| 2003/0154189 A1 | 8/2003 | Egilsson et al. | |
| 2003/0163461 A1 | 8/2003 | Gudbjartsson et al. | |
| 2003/0224394 A1 | 12/2003 | Schadt et al. | |
| 2003/0229451 A1 | 12/2003 | Hamilton et al. | |
| 2004/0030578 A1 | 2/2004 | Cross et al. | |
| 2005/0197783 A1* | 9/2005 | Kuchinsky et al. ........ | 702/19 |
| 2007/0286218 A1* | 12/2007 | Zhang et al. .......... | 370/401 |

\* cited by examiner

*Primary Examiner*—Carolyn L. Smith
(74) *Attorney, Agent, or Firm*—Price, Heneveld, Cooper, DeWitt & Litton, LLP

(57) ABSTRACT

A system and method for performing a research and analysis in the bioinformatics field which associates data from a variety of experimental platforms with preclinical and/or clinical samples and subjects. The system and method allows for the analysis of data stored therein received from a variety of experimental platforms, as well as association with preclinical and clinical sources. A fully integrated medical informatics/molecular bioinformatics database/analysis package is provided herein suitable for accelerated target discovery, diagnosis, and treatments for molecular-based diseases. An identified relationship is used with a computational distribution for scoring nodes in a network built from a set of experimentally-derived condition-specific genomic or proteomic profiles for the development of new treatments, diagnoses, biomarker identification, or target identification. The biomedical research tool provides for multi-directional data directionality that allows for detailed genotype to phenotype analysis for the evaluation of new drugs and treatments.

5 Claims, 7 Drawing Sheets

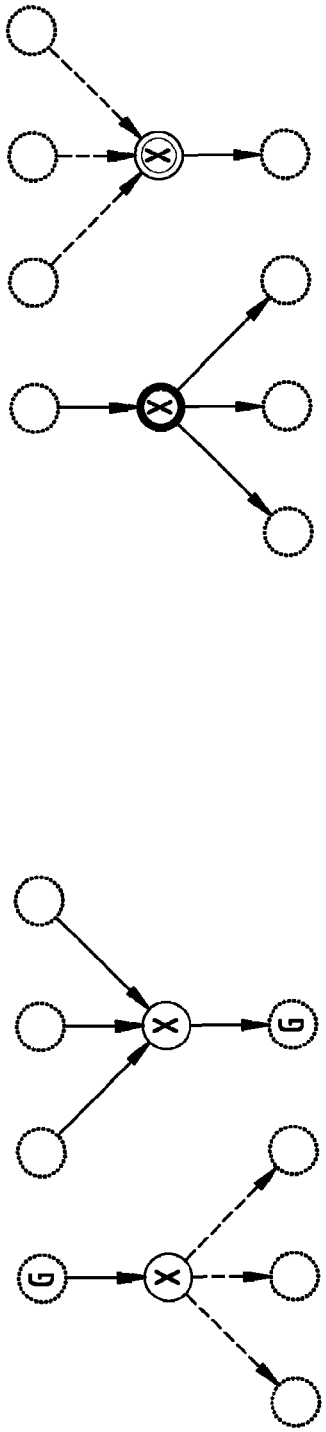
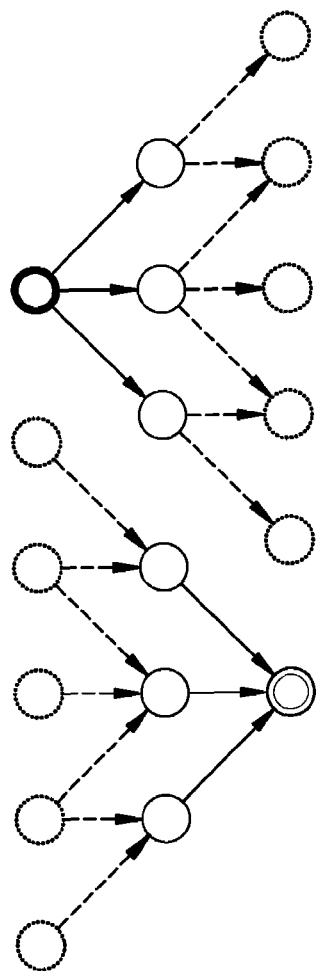
FIG. 6A
FIG. 6B
FIG. 6C

BIOINFORMATICS RESEARCH AND ANALYSIS SYSTEM AND METHODS ASSOCIATED THEREWITH

CROSS-REFERENCE TO RELATED APPLICATION

This application claims priority under 35 U.S.C. §120 and is a continuation-in-part of U.S. Patent application Ser. No. 11/186,091 filed Jul. 21, 2005 now abandoned entitled BIOINFORMATICS RESEARCH AND ANALYSIS SYSTEM AND METHODS ASSOCIATED THEREWITH, which is a continuation of U.S. patent application Ser. No. 11/084,290, filed Mar. 18, 2005 now abandoned entitled BIOINFORMATICS RESEARCH AND ANALYSIS SYSTEM AND METHODS ASSOCIATED THEREWITH, which claims priority from U.S. Application No. 60/554,295 filed Mar. 18, 2004 entitled BIOINFORMATICS RESEARCH AND ANALYSIS SYSTEM AND METHODS ASSOCIATED THEREWITH, which are all commonly assigned to the Van Andel Research Institute and all herein incorporated by reference in their entirety.

FIELD OF THE INVENTION

The present invention relates generally to a system and method for performing a research and analysis in the bioinformatics field which associates data from a variety of experimental platforms with preclinical and/or clinical samples and subjects.

BACKGROUND

Whilst there are numerous stand alone software or database packages suitable biomedical research, there are none that integrate phenotype and genotype analysis into a single system with two-way directionality and functionality. There is no way for which medical informatics can feed necessary information into a bioinformatics (molecular-based) system that utilizes clinical data together with molecular information to establish meaningful clinical/preclinical applications of molecular-based medicine. Because of specific needs of clinicians, animal care technicians, molecular-based scientific researchers, pharmaceutical researchers, etc., no system exists to integrate these overlapping needs into a single system with multiple applications. The vision is that the respective features required by different disciplines will have to be integrated at some point, particularly as molecular-based research moves ever closer to clinical application. Moreover, through the combination of medical informatics and molecular informatics, the discovery of new diagnostics and treatments is greatly accelerated.

Currently, researchers are forced to study a small subset of "clinical phenotypes" based upon their bias, and ask whether molecular data can be fitted to their phenotypes of interest. Conversely, clinicians are devoid of access to simple, meaningful (clinically applicable) but novel molecular diagnostics/treatment strategies for the future. Within the pharmaceutical industry, vast amounts of data are accumulated throughout the drug discovery process within different sectors (such as target discovery, drug discovery, preclinical and clinical groups) using a variety of experimental platforms. This requires an integrated solution that comprises database and analysis tools that allow for multiple users in different disciplines to utilize a common informatics solution such that data can be exchanged and shared along the drug discovery pipeline in a meaningful fashion.

There have been no public attempts to develop an equivalent fully integrated solution. As mentioned above, there are many individual "modules" for various sub-problems, but little in the way of conjoining these modules, and nothing on utilizing this functionality. Typically, databases have been designed that may track subjects and samples and associated data, but do not allow for analysis of the data within the same structure. Typically, data files must be exported to secondary software (such as GeneSpring, Spotfire) that performs various statistical analyses and generates "molecular results." As such, there are no means by which the molecular results can then be exported back into the database, to extract the subject/sample/experimental parameters that may explain the molecular results (i.e., a so-called "hypothesis").

Moreover, while systems biology tools and approaches are gaining wide acceptance among molecular biologists and clinical researchers, two fundamental issues have emerged. The first one is how to use sets of available high-throughput molecular data to reconstruct biological networks that are truly relevant to the condition of interest. The second, even more important issue is how to utilize results of such reconstruction in the framework of standard laboratory practices and in clinical applications. In a typical pathway analysis set-up the first step is association of experimentally identified genes and/or proteins with available pathway and protein interaction data. When reconstructing condition-specific networks it is often assumed that groups of proteins responsible for performing certain biological functions should be closely located in terms or "network distance." Thus different variations of the "shortest path" algorithm often serve to extract such modules. The algorithms are usually accessible either as built-in network reconstruction tools within commercial software packages or as open-source plug-in modules for Cytoscape. However, one fundamental issue facing this approach is the fact that biological networks are highly interconnected due to the presence of a small number of hubs—network nodes with hundreds or even thousands of connections. Thus, almost under any circumstances, the shortest path between two nodes would be the one via such hub(s). Even though this may, in some cases represent biologically meaningful pathways, many network modules constructed in this way would actually be artifacts. Thus, further analysis of network topology and graph statistics are needed to find pathways that are truly significant for a given molecular profile.

Few attempts have already been made to address this issue where others have proposed to weigh nodes in metabolic networks based on their connectivity were a penalty is assessed to highly connected metabolites. These types of results show significant improvement in the accuracy of predicting known metabolic pathways. Another approach, uses well-established canonical pathways as "shortcuts" while generating shortest paths in protein signaling networks. These types of algorithms give preference to known signaling routes while reconstructing condition-specific networks. In another recent research, the emphasis has shifted from high degree hubs to nodes that are "bottlenecks" in the network—those that have disproportional number of shortest paths going through them. While these improvements indeed lead to selection of many biologically meaningful pathways—they do not consider network topology in the context of a particular molecular profile. For example, penalizing hubs might exclude them in situations where they play a truly important role in a condition-specific network. By the same token, always giving preference to known pathways limits the ability to generate new hypothesis about important signaling cascades.

A second and even more important issue is how to utilize results of the systems-level analysis in guiding further laboratory research and clinical applications. The results of pathway analysis are usually sets of fairly complex networks or sets of functional processes that are deemed to be relevant to the condition represented by the molecular profile. While this information is certainly useful, due to the nature and limitations of work in the research or clinical laboratory one still needs to make the transition back to the level of verifiable hypotheses about roles of individual genes and proteins. Thus, the problem of guiding further research often requires identifying a relatively small number of molecules that can be further interrogated in the laboratory with clear-cut outcomes allowing either to confirm or refute a hypothesis.

BRIEF DESCRIPTION OF THE FIGURES

FIGS. 6A, 6B, and 6C are diagrams illustrating different connectivity patterns of significant nodes.

Figure 1:
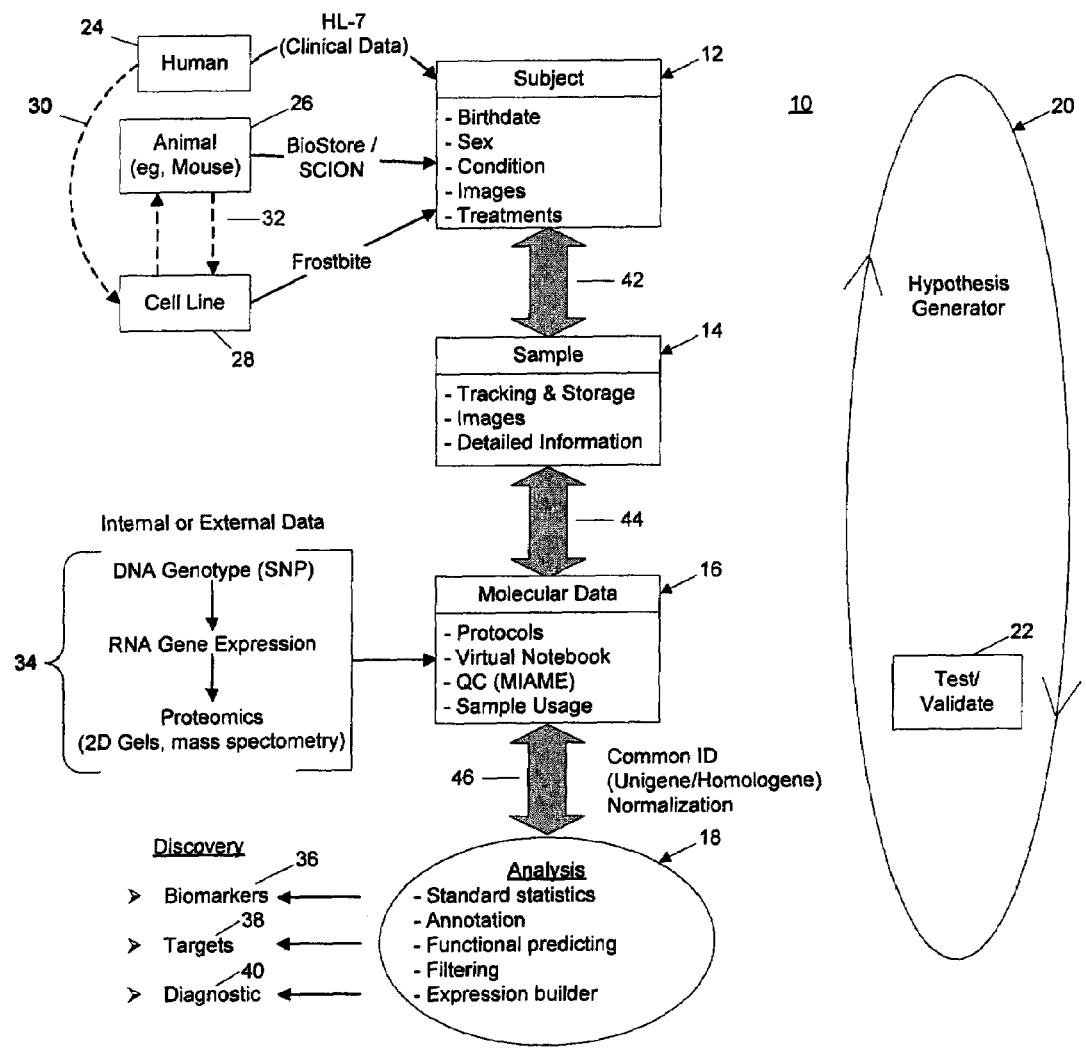
FIG. 1 is a flowchart diagram illustrating a conceptual overview of the bioinformatics system and method showing the interaction between subject, sample, molecular data, and analysis tools provided in the inventive system and method described herein.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF THE PREFERRED EMBODIMENTS

Before describing in detail embodiments that are in accordance with the present invention, it should be observed that the embodiments reside primarily in combinations of method steps and apparatus components related to bioinformatics research and analysis system. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

With reference now to the drawings, and to FIG. 1 in particular, a biomedical research tool 10 is shown in flowchart form which comprises, among other things, a subject storage unit 12, which may optionally include a sample storage unit 14, a molecular data storage unit 16 and an analysis module 18. While it will be understood that the inventors have determined that the subject storage unit 12, sample storage unit 14 and molecular data storage unit 16 are preferable types of data to be collected with the biomedical research tool 10, it will also be understood that additional and/or less data or different types of data can be collected without departing from the scope of this invention and the types of data collected should not be interpreted as limiting on the scope of this invention.

The storage units 12-16 and the analysis module 18 are operably interconnected to a hypothesis generator 20 which includes within it a testing/validation component 22 which is used for testing a validating hypotheses generated by the hypothesis generator 20 which will be further described below. The subject storage unit 12 will now be described in greater detail and can take the form of, for example, a table in a database or other suitable storage unit for semi-permanent maintenance and storage update of records which would be apparent to one skilled in the art. The subject storage unit 12 can include data representative of entities upon which the analysis and research functions of the biomedical research tool 10 are performed and can include, but are not limited to, entities such as patients, animals, and/or cell lines from which molecular data are derived and/or samples for further experimentation and analysis can be collected.

Examples of information representative of the subjects contained in the subject storage unit 12 can include clinical and/or phenotype information such as date of birth, sex, condition (e.g., disease state and/or stage), images such as radiological exams, voice files such as medical dictation files, or any related text and/or data files, and treatment information. This information can be received by the subject storage unit 12 in different ways. For example, data can be manually entered, or it can be automatically extracted from external sources. One example of external source for human subject information is shown by reference numeral 24, and is shown schematically as a data transfer and arrow directed from the external human subject information 24 to the subject storage unit 12 and can take the form of a data stream from the well-known HL-7 clinical data source, which is a medical informatics system containing wide range of data representative of human patients from clinical and/or research sources. Another external source is shown interconnected to the subject storage unit 12 and is shown as external animal subject information and identified by reference numeral 26. The external animal subject information is shown by example as information received from an external animal subject information source 26 such as BioStor as used by the Van Andel Institute, Grand Rapids, Mich., or from SCION, which is an external mouse-tracking data source which has various types of preclinical and/or research information.

The subject storage unit 12 can also include data from an external cell line information source which is shown by reference numeral 28, which contains information representative of a cell line obtained from a subject source (as the term subject is used herein). Cell lines are tissue material obtained from a subject that are cell grown in culture from the subject and stored externally of the subject upon which future experimentation and analysis can be performed. In addition, cell lines are frequently transplanted back into an experimental subject (a/k/a "xenograft"), as indicated by the arrow joining cell line module 28 to the animal module 26. This feature allows for the tracking of xenograft experiments.

It is important to maintain a link between the particular subject cell line stored in the subject storage unit 12 and the particular subjects from which they came. Therefore, linkage information is also maintained within the subject storage unit 12 which identifies a particular cell line and the particular subject (e.g., human or animal source) from which it came. This parental linkage information is shown by reference numerals 30 and 32 in FIG. 1. For example, the human parental linkage 30 identifies the particular human from which a cell line was obtained from and reference numeral 32 identifies a particular animal from which a particular cell line came from. It will also be understood that the subject storage unit 12 also tracks all types of relationships between subjects, samples and other information which will be further described below. Examples of these relationships include parent-child, sample and sub-sample, and other pedigree and tracking information which would be apparent to one skilled in the art in the clinical and/or laboratory setting.

The sample storage unit 14 will now be described in greater detail. The sample storage unit 14 can comprise a table containing database records or other suitable storage unit for semi-permanent maintenance and storage update of records which would be apparent to one skilled in the art. The sample storage unit 14 contains data representative of any type of sample obtained from a particular subject as stored in the subject storage unit 12. Examples of samples can include blood samples, tissue samples, biopsies, cell line treatments, urine samples, fecal samples, and other types of tissue and biomedical samples which would be apparent to one skilled in the art and that are typically collected for medical and biomedical analysis.

Various exemplary types of information stored in the sample storage unit 14 can include tracking information with respect to a particular sample, storage information, links and/or data files containing images and other data representative of the sample, and other detailed information which would be apparent to one skilled in the art and that are typically collected in a laboratory and/or research setting. Other information can include the pedigree and relationship tracking information mentioned above. The molecular data storage unit 16 will now be described in greater detail and can take the form of, for example, a table in a database or other suitable storage unit for semi-permanent maintenance and storage update of records which would be apparent to one skilled in the art. Various types of information stored in the molecular data storage unit 16 can include protocols representative of typical steps performed in experimental and/or molecular analysis, virtual notebooks typically maintained by researchers in a laboratory setting, quality control (such as, for example, data and/or information representative and complying with the MIAME standard which would be apparent to one skilled in the art), and sample usage information which is representative of tracking and usage information of how much of a particular molecular sample was used in a particular experiment and allowing the researchers to track the remaining amounts of a sample available for further analysis.

Different types of molecular data can be stored in the molecular data storage unit 16 and/or identified in FIG. 1 by reference numeral 34 and can comprise, but are not limited to, DNA genotype (such as single nucleotide polymorphisms commonly identified with the abbreviation SNP), RNA expression information, and proteomic information such as that obtained from commonly-available research tools such as 2-D gels and mass spectrometry. The arrows between the various types of molecular data 34 are simply representative of the various levels of molecular information and/or the natural flow of information and molecular biology from DNA to RNA to protein level analysis. These arrows are shown to identify the capability of the biomedical research tool 10 to handle any level of molecular data and store that type of molecular data in the molecular data storage unit 16. It will be understood that other types of molecular data can be stored within the molecular data storage unit 16 without departing from the scope of this invention and the particular example types of molecular data 34 shown in FIG. 1 should not be interpreted as limiting on the scope of this invention.

The analysis module 18 will now be briefly described. The analysis module 18 is operably linked to the subject storage unit 12, the sample storage unit 14, and the molecular data storage unit 16 and is capable of obtaining raw and/or filtered and/or normalized data from these storage units and performing detailed analysis on received data from these storage units 12-16. The analysis module 18 also has a detailed filtering module which will be further described with respect to an example user interface below. Examples of the type of analysis performed by the analysis module 18 include, but are not limited to, standard statistical analysis, annotation, and/or functional predicting.

The leftward-directed arrows adjacent to the analysis module 18 in FIG. 1 are representative of output of the analysis module 18 which are useful in the discovery of biomarkers 36, targets 38, and diagnostics 40. Biomarkers 36, as would be generally known to someone skilled in the art, are indicators of a current medical state, such as a medical condition or response to a treatment (e.g., such as how the prostate-specific antigen commonly abbreviated as PSA is useful in the identification and/or indication of a prostate cancer condition).

Targets 38, as the term is generally used to one skilled in the art, are genes, genetic entities and/or molecular entities that are suitable for future drug development and are identified as suitable goals for future experimentation as an entity that may respond to drug and/or other medical treatment. Diagnostics 40, as the term would be familiar to one skilled in the art, are tools used during the accurate diagnosis of a medical condition and can be used for the identification and/or treatment of a medical condition. All three of these elements (biomarkers 36, targets 38, and diagnostics 40) can be readily identified by the analysis module 18 in a manner that will be further described below. In addition, it will be understood that while the terms biomarkers, targets, and diagnostics are used herein, there can be substantial overlap between these three elements in the data and output identified by the analysis module 18. Further, it will be understood that other medical diagnosis, research and drug development data can be obtained from the analysis module 18 even though they are not specifically noted in FIG. 1.

As can be seen from FIG. 1, the subject storage unit 12, sample storage unit 14 and molecular data storage unit 16, as well as the analysis module 18, are interconnected by suitable data linkages as represented by the double-headed arrows in FIG. 1 which show the two-way passage of data between these storage units and the analysis module 18. For example, the subject storage unit 12 and the sample storage unit 14 are interconnected by a subject-sample linkage 42, the sample storage unit 14 and the molecular data storage unit 16 are interconnected by a sample-data linkage 44, and the molecular data storage unit 16 and the analysis module 18 are interconnected by a data-analysis linkage 46.

It will be understood that these data linkages between the particular storage units 12-16 and the analysis module 18 are shown by example only, and other modes and methods of passage of data between these storage units 12-16 and the analysis module 18 can be made without departing from the scope of this invention and which would be apparent to one skilled in the art. As which will be further described, this two-way passage of information is important because the hypothesis generator 20 obtains information from the storage units 12-16 and the analysis module 18 and the two-way passage of data between these storage units and the analysis module 18 provides for efficient and speedy transfer of data for the hypothesis generator 20.

This two-way passage of information is also useful in the functionality of the hypothesis generator 20 because, as contrasted with prior research tools, the two-way passage of information allows the hypothesis generator 20 to perform and generate data representative of its hypotheses and test and validate that information based on the data stored in the storage units 12-16 and as modified by the analysis module 18, and then allows for further development of those hypotheses based on further testing and validation on data subsequently received in the storage units 1216. This functionality of the hypothesis generator 20 will be further described below. The data-analysis linkage 46 between the analysis module 18 and at least the molecular data storage unit 16 and, optionally, between the subject storage unit 12 and the sample storage unit 14, modified the data from the storage units 12-16 into a state suitable for the functions performed by the analysis module 18. The various modifications performed by the data-analysis linkage 46 include, but are not limited to, generation of common identifiers between external molecular data sources (such as UniGene and Homologene, as well as other standardization of linkages between external data sources representative of gene information and that contained within the biomedical research tool 10).

It will be understood that, for the purposes of this invention, the terms gene, molecular data, and protein can be commonly referred to herein by the term molecular information and/or genetic information and the particular terms used to describe genes, DNA, RNA, and proteomic information should not be interpreted as limiting on the scope of this invention as these terms can be used in their commonly accepted sense and under a common umbrella of the terms molecular information and genetic information as used herein. Other types of functions performed by the data-analysis linkage 46 include normalization of data for the purpose of standardizing data contained in different scales in units so that these different data values can be compared on a common scale. Other types of data conditioning and preparation can also be performed without departing from the scope of this invention.

Figure 2:
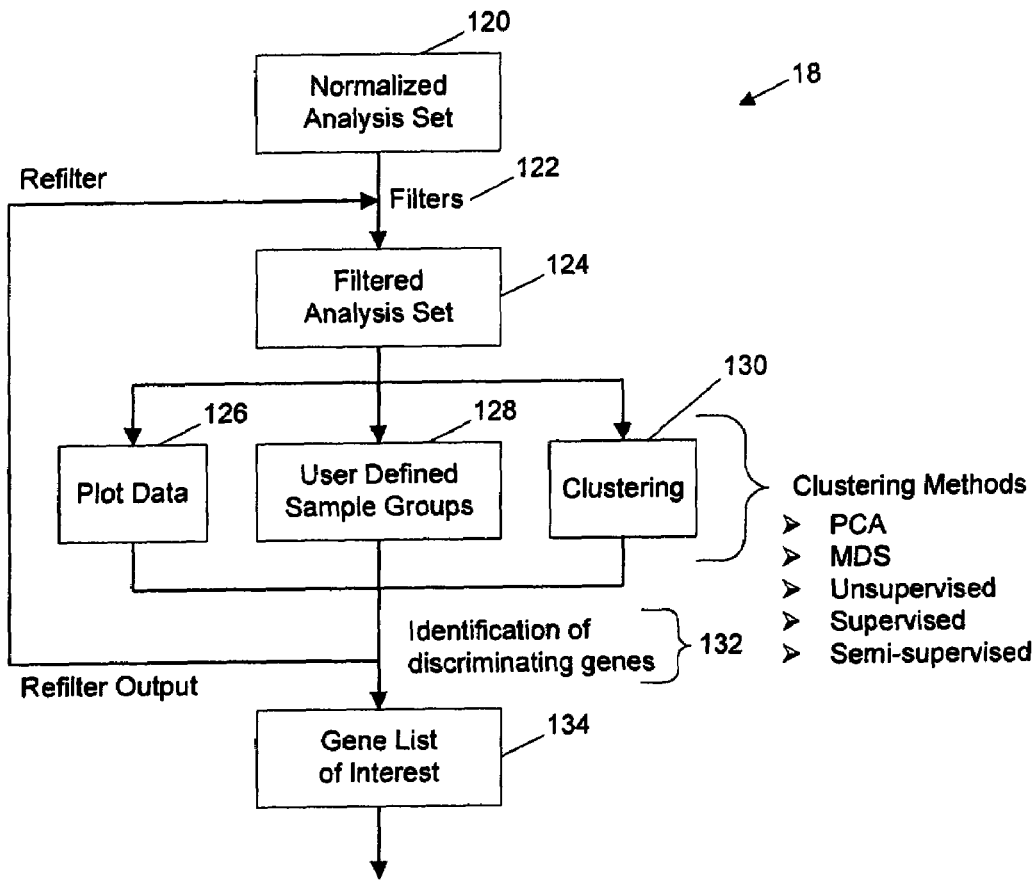
FIG. 2 is a flowchart diagram showing data that has been extracted and normalized which is thereafter optionally filtered by the user.

FIG. 2 is a flowchart diagram showing data that has been extracted and normalized which is thereafter optionally filtered by the user. Once a normalized analysis set 120 has been defined from the user-defined criteria, the normalized analysis set 120 is passed to the analysis module 18. With specific reference to FIG. 2, the normalized analysis set 120 can thereafter be subjected to user-defined filters 122 to result in a filtered analysis set 124. The filters 122 can be any suitable data selection and/or data limiting mask applied to the normalized analysis set 120. It will be understood that the filters 122 can be platform-independent for filters which are common to any incoming normalized analyzed set 120 while other filters 122 can be platform-dependent and are specific to a particular normalized analysis set 120 which is received by the analysis module 18. Various examples of filters 122 which can be applied to the normalized analysis set 120 include, but are not limited to, filters which relate to the presence of a gene in a particular number of samples, intensity filters relating to intensity results relating to the magnitude of a particular data value, and other more specialized filters such as fold-change and specialized proteomics filters which will be described in greater detail below. It will be understood that additional and/or fewer filters 122 can be present without departing from the scope of this invention. It will also be understood that the filtered analysis set 124 can be identical to the normalized analyzed set 120 if the user chooses not to apply a filter 122 to the normalized set 120.

The filtered analysis set 124 is then passed to a variety of statistical analysis tools as selected by the user of the biomedical research tool 10. Examples of the various analysis tools provided within the analysis module 18 are shown in FIG. 2 and include, but are not limited to, plotting data relating to the filtered analysis set 124 shown by reference numeral 126, a user-defined sample group step 128 which enables a user to select subsets of the filtered analysis set and compare those groups to one another in both data-lists and diagrammatical visual outputs, and a clustering step 130 which enables a user to group subsets of the filtered analysis set 124 according to various general and/or user-selected clusters. It will be understood that the clustering step 130 can be performed by any number of well-known algorithms, some of which are set forth in FIG. 2, such as principle component analysis (PCA), multi-dimensional scaling (MDS), hierarchical clustering, such as well-known unsupervised and supervised clustering algorithms, and semi-supervised hierarchical clustering algorithms, such as K-means and the like.

In any event, the biomedical research tool 10, though the analysis module 18, funnels output of the various analysis tools, such as those shown by reference numerals 126-130 in FIG. 2 into a discriminator 132 which identifies both groups and molecular information (e.g., genes) which define those groups which have potential for enabling discovery of further molecular information, such as those outlined in FIG. 2-1 relating to the discovery of items such as biomarkers 36, targets 38, and/or diagnostic information 40. The desired output of the analysis module 18 is a gene list of interest identified in FIG. 2 by reference numeral 134.

Figure 3:
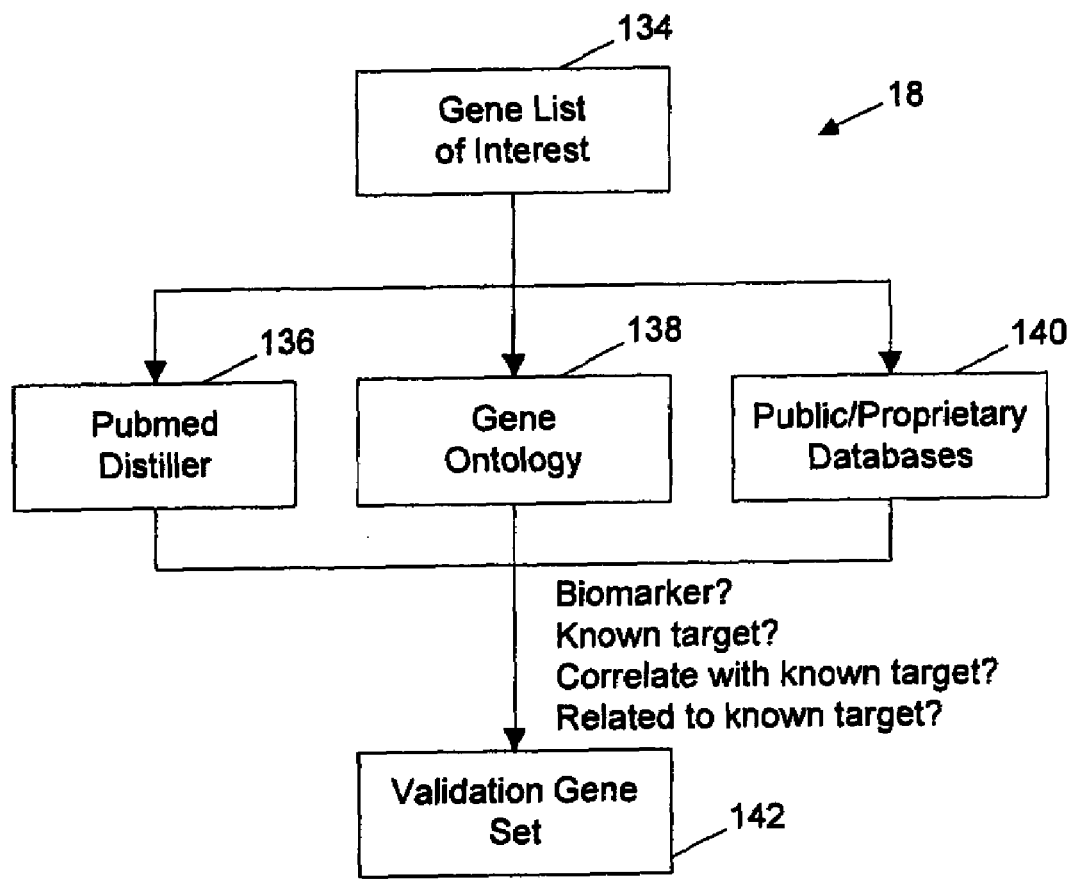
FIG. 3 is a flowchart diagram showing a gene listed as collected according to the method described with respect to FIG. 2 illustrating various ways of annotating the gene list with information from various sources.

FIG. 3 is a flowchart diagram showing a gene listed as collected according to the method described in FIG. 2. While the gene list of interest 134 can be passed directly to an annotation mechanism as shown in FIG. 3, the gene list of interest 134 can also be saved and applied as a filter 122 to another normalized analysis set 120 produced by the user of the biomedical research tool 10. This allows one gene list of interest 134 produced with a first normalized analysis set 120 to be applied as a filter 122 to another normalized analysis set 120 to allow for cross-checking and validation between data sets whether independent or produced from a common source. The feedback loop between the gene list of interest 134 and the filters 122 in FIG. 2 represents this ability to apply one gene list of interest 134 to another normalized analysis set in a different session of use of the biomedical research tool 10. In addition, the output of the analysis tools 126-130 into the discriminator 132 can also be applied and re-filtered as shown in the feedback loop between items 132 and the filters 122 in FIG. 2 as well.

In further discussion of the concept of saving a gene list of interest 134 for later use, the biomedical research tool 10, through the analysis module 18, permits a user to save multiple gene lists (and for that matter, multiple users can save multiple gene lists), and the analysis module permits a user to compare and conceptually overlap multiple gene lists of interest 134 to find common subject matter between the multiple-saved gene lists of interest. The biomedical research tool 10 through the analysis module 18, which will be further described below, also permits visual display of such overlapping subject matter as well as a "drill down" display of a table of overlapping subject matter from a visual display of such overlapping subject matter, such as through a Venn diagram. It will be understood that the gene list of interest 134 can be generated through the analysis module 18 from a normalized analysis set 120 as has been previously described or, as is permitted by the biomedical research tool 10, a gene list of interest 134 can be imported from an external source and in a suitable format.

Once the user has identified a gene list of interest 134, it has been found to be desirable to prepare the gene list of interest 134 to determine whether the genes contained within the gene list of interest 134 have previously been implicated in the desired research analysis target that the user is using the biomedical research tool 10 for. This preparation step can assist in a determination of which genes contained in the gene list on interest 134 have previously been validated or have been shown to be important for the research goals during use of the biomedical research tool 10. One of the ways in which a gene list of interest 134 can be validated is by comparison to prior published work on the subject matter and by review of publicly available information. Another inventive way in which a gene list of interest 134 is validated using the biomedical research tool 10 is by collecting additional experiment data as suggested by hypothesis. In addition, the validation and annotation steps shown in FIG. 3 are helpful in grouping and clustering various genes contained in the gene list of interest 134 and using previously-validated subsets of genes contained in the gene list of interest 134 for identification and prediction of associated and/or related genes also contained in the gene list of interest 134 and by associating the genes contained in the gene list 134 with previous associations contained in prior publications.

As seen in FIG. 3, various ways of annotating the gene list 134 with prior publications and prior work are shown. For example, the gene list of interest 134 can be correlated with published information in the PubMed database available from the National Library of Medicine (NLM) and indexed in a high-speed manner using a PubMed distiller in accordance with the invention as identified by reference numeral 136. The gene list of interest 134 can also be validated by examination of publicly-available gene ontology information as identified by reference numeral 138. The gene list of interest 134 can also be validated by association and correlation with public and/or proprietary data base as identified by reference numeral 140. For example, a user of the biomedical research tool 10 can provide a proprietary database in a standard format which can be linked to the biomedical research tool 10 and gene research and correlation information contained within the proprietary database can be used to validate the produced gene list of interest 134. Further, the gene list of interest 134 can also be validated with respect to publicly-available database information such as the public microarray database available from Stanford University, which would be apparent to one skilled in the art. Publicly-available validation information can also be available from the National Center for Biotechnology Information (NCBI), which has publicly available expression database for use as well, use of which would be apparent to one skilled in the art. It will also be understood that a myriad of other public and proprietary databases 140 are available, and the particular examples of public and proprietary databases discussed with respect to FIG. 3 should not be construed as limiting on the scope of the invention.

Once the gene list of interest 134 has been validated with respect to the exemplary annotation sources, such as the PubMed distiller 136, gene ontology information 138, and public/proprietary database 140, as shown in FIG. 3, a user of the biomedical research tool 10 can examine the annotated gene list of interest 134 and determine whether genes contained in the gene list of interest have been previously identified as suitable biomarkers, known drug targets, whether they correlate with known targets, and whether they are related to known targets. The resulting analysis performed with respect to FIG. 3 is a validation gene set which is identified by reference numeral 142. The validation gene set 142 can be provided for laboratory analysis to determine whether the gene set identified with respect to FIG. 3 functions as expected. This can be used to identify potential future treatments and used as a diagnostic tool.

The gene list of interest 134, can potentially contain thousands of genes from the output of the methods shown in FIG. 2. The number of genes can be reduced through the annotation and validation to a highly relevant set contained in the validation gene list 142 which has one of two functions using the biomedical research tool 10. First, the validation gene set 142 can be provided to an open "wet lab" for further validation on whether the validation gene set 142 indeed contains relevant genes for the research goals of the user. Second, the validation gene set 142 can also be employed by the biomedical research tool 10 and used as a predictor of classification of phenotype information. The annotation and validation steps shown in FIG. 3 essentially tells a user of the biomedical research tool 10 what is publicly and previously known about genes contained in the gene list of interest 134 and whether those genes have been implicated in phenotype of interest relevant to the users research goals. In addition, the biomedical research tool 10 can use the validation gene set 142 to make a prediction about the function or role of genes within the validation gene set 142. In this manner, genes within the validation gene set 142 can be sub-divided into sets of genes having either known functions and implications or unknown functions and implications and whether genes contained within the reference list can be clustered into known sets.

Figure 4:
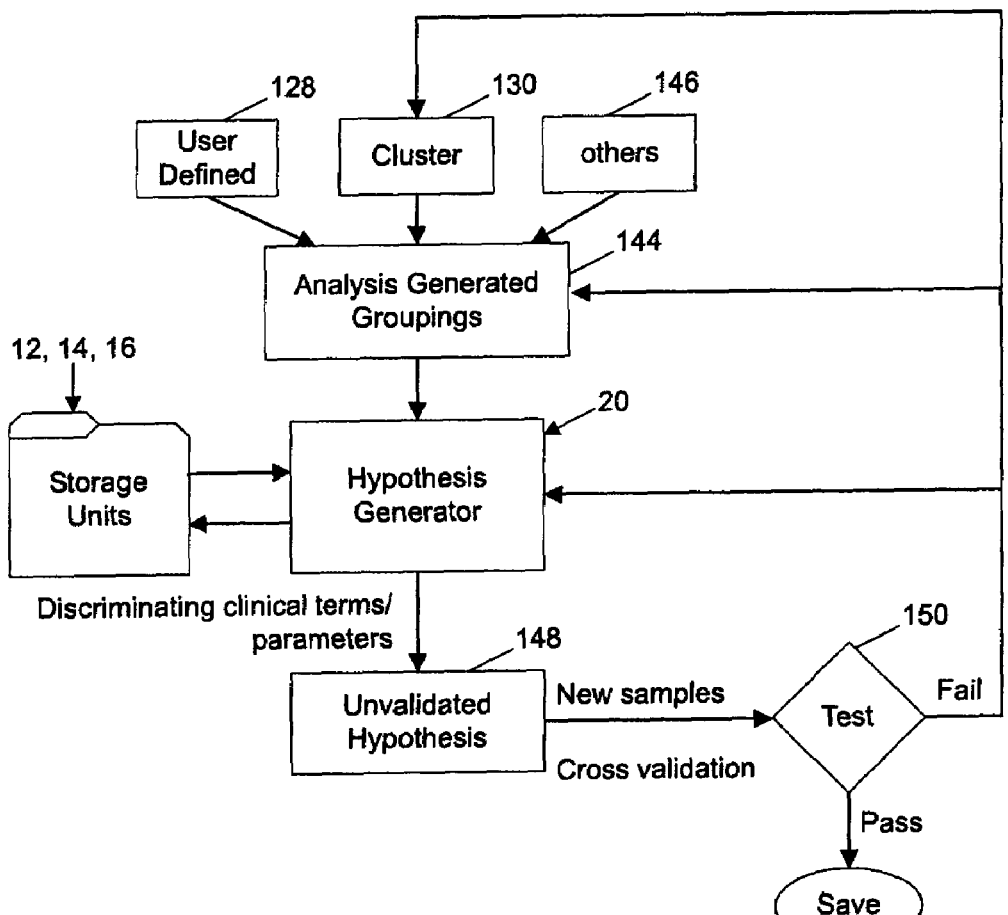
FIG. 4 is a flowchart diagram of a hypothesis generator module of the inventive system and method as shown in FIG. 1.

FIG. 4 is a flowchart diagram of a hypothesis generator module 20. In operation, the analysis module 18 can take a filtered analysis set 124 and create a gene list of interest 134 through various analytical tools such as those shown by reference numerals 126, 128, and 130. Another output of the analysis module, for example, the analysis tools of the user-defined sample groups 128 and the clustering 130 can produce analysis-generated groupings as shown by reference numeral 144. In addition, the analysis-generated groupings can be generated by other inputs 146 (including, but not limited to, statistically calculated groups), which would be apparent to one skilled in the art. The analysis-generated groupings 144 are user-defined groups or groupings of the raw data output of the analysis module 18 based on generally available statistical tools to create groups of records output from the filtered analysis set. The groupings contained in the analysis-generated groupings 144 are typically based on the molecular data contained in the filtered analysis set 124.

The hypothesis generator 20 receives the analysis-generated groupings 144 and determines which phenotypes stored in the storage units 12-16 correlate with the various groupings contained in the analysis-generated groupings 144. The analysis generated groupings 144 generally contain genotype information which, as described above, are the molecular data contained in the filtered analysis set 124. As shown in FIG. 4, the raw data contained in the filtered analysis set 124 is fed into the analysis tools such as those shown by steps 128, 130, and 146, and which the analysis-generated groupings 144 are created therefrom. The hypothesis generator 20 then takes the raw molecular data contained in the analysis generated groupings 144 and determines which phenotypes correlate with the genotype information contained in the analysis-generated groupings 144. In order to determine which phenotype information correlate with the genotype information contained in the analysis-generated groupings 144, the hypothesis generator 20 searches the storage units 12-16 and, more particularly, the subject storage unit 12 and the sample storage unit 14 for phenotype information which correlate to the genotype information contained in the analysis-generated groupings 144. The molecular data storage unit 16 is also searched to identify possible confounding experimental variables that correlate with the observed groupings.

The hypothesis generator 20 represents a great advance over scientific and biotechnology related research methods of the past. Previously, a researcher would come up with his/her own hypothesis regarding a single phenotype-genotype relation, e.g. which single phenotype relates to a particular genotype. For example, whether age or height or gender was a factor in a particular genetic condition such as colon cancer. The researcher would then perform extensive research attempting to correlate the researcher-selected phenotype with the particular genotype. If the hypothesis proved wrong, the researcher would have to start over. The hypothesis generator 20 is a fully automated means which operates in the reverse direction that traditional research has operated in.

Whereas traditional research has operated from the phenotype-to-genotype direction, the hypothesis generator operates in reverse. Specifically, the hypothesis generator 20 operates in the genotype-to-phenotype direction in which groupings of particular genotype-related information are statistically determined independent of any related user bias hypothesis and these groupings are then correlated to phenotype-related information contained in the subject and sample storage units 12 and 14, and the molecular data storage unit 16, and any associated experimental data files 96 to correlate phenotype information to the statistically- and independently-grouped genotype information contained in the analysis-generated groupings 144. By allowing a user to select a set of data from the biomedical research tool 10, such as that shown in the filtered analysis set 124, and then statistically grouping the genotype information in the analysis-generated groupings 144, a researcher can perform hundreds, if not hundreds of thousands, of genotype-related associations and groupings without requiring independent permutation and combination of each.

Namely, by allowing the statistically-independent groupings 144 to form the basis for the hypothesis generator 20, a researcher is provided with an output list of phenotypes which have underlying genotypic causes. In summary, the hypothesis generator outputs one or more hypothesis which contain at least one, and typically several, positive and/or negative phenotype associations with the particular genotype-related analysis generated groupings 144. This is a great advance over previous research techniques since the researcher is not required to preconceive a particular phenotype-based hypothesis and determine whether that phenotype-based hypothesis is correct after months of research. Rather, the hypothesis generator outputs all determined phenotype-related hypothesis which result from the particular genotype-related analysis-generated groupings 144.

The hypothesis generator 20 exposes a fallacy in phenotype-related research to date. Since genotype dictates phenotype, it is an important feature of this invention that the basis of hypothesis stem from genotype-related groupings, not phenotype-based hypothesis which are artificial at best, since without extensive research to confirm that the phenotype is even related to the genotype in the first place. The hypothesis generator 20 represents a significant advancement over previous phenotype-based hypotheses which can be driven potentially by independent investigators' personal bias. The hypothesis generator produces an unbiased, statistically significant association between genotypes and particular analysis generated groupings 144 with phenotype information contained in the storage units 12-16 and potentially associated experimental data files 96. It is important to note that hypothesis testing and cross validation can be carried out on a user-specified hypothesis independent of the hypothesis generator function offered by the biomedical research tool 10. In this case, the user selects groups based upon their preconceived hypothesis, and the biomedical research tool then performs discrimination analysis and cross validation as described below.

The hypothesis generator 20 is capable of producing an output of phenotype-related hypothesis (or multiple hypotheses) corresponding to a particular genotype grouping 144 in view of its close association between molecular data and the phenotype information contained in the storage units 12-16. While the experimental data contained in the molecular data storage unit 16 is not necessarily phenotype based, it can also be used as a basis for the output of the hypothesis generator 20 because experimental data and variables can affect the experimental results. This provides a desirable level of quality control to the output of the hypothesis generator 20. For example, if it is determined from the output of the hypothesis generator 20 that experimental data variables have become significant in the results, it is desirable to return to the experiment 94 itself and introduce additional controls into the experiment to eliminate variants introduces by the experiment 94.

The hypothesis generator outputs one or more unvalidated hypotheses, which are identified by reference numeral 148, which identifies, while untested, which phenotype information discriminate with respect to the inputted analysis-generated groupings 144 (which are genotype-based). At a minimum, the outputted unvalidated hypothesis 148 determines which phenotype (e.g., clinical terms and/or parameters) corresponds to the particular statistical groupings of the genotype inputs in the groupings 144. In order for the hypothesis 148 made by the hypothesis generator 20 to be evaluated and/or validated, further steps may be performed. At this point in use of the inventive systems and methods described herein, the produced unvalidated hypothesis 148 represents an untested and unvalidated hypothesis which corresponds only to the inputted statistical genotype groupings 144. Next, the unvalidated hypothesis 148 can be compared to new samples entering the storage units 12-16, and/or experimental data test files 96 to determine whether the hypothesis 148 generated by the hypothesis generator 20 confirms the hypothesis that was generated.

In order to test the unvalidated hypothesis 148, additional independent samples are identified within the storage units 12-16 that meet certain criteria displayed by the first set of samples used to generate a hypothesis. The corresponding data files for these test samples are then used to test the hypothesis using cross validation statistics. If the unvalidated hypothesis 148 passes the statistical cross-validation test shown at decision point 150 with regard to additional samples within the biomedical research tool 10, the hypothesis (genotype=phenotype) is saved in the biomedical research tool 10 and is used for continued comparison with future samples. If the test at decision point 150 fails, processing returns to the hypothesis generator 20, analysis generated groupings 144, or analysis tools 128, 130, or 146, to produce a new unvalidated hypothesis 148 from additional samples and/or analysis.

With respect to identifying patterns (hypotheses) within the complex clinical and molecular datasets that could be translated into clinical diagnostic applications, unsupervised clustering techniques are used, such as hierarchical clustering. In this fashion, sample similarity with respect to clinical, experimental, and/or molecular attributes can be assessed where biomedical research tool 10 extends these analyses to identify clinical and/or experimental variables that statistically correlate with defined sample sub-groups. During this step of hypothesis generation, biomedical research tool 10 runs back into the database housing all of the standardized clinical and experimental data and identifies correlates of the selected sub-groups. This is a highly powerful utility when operating in unsupervised mode, and requires an intricate link between data analysis and database content. Unsupervised clustering may, for example, identify the degree of molecular similarity across a cohort of patient samples, which could identify several clearly delineated groups at the genotype level. Running in hypothesis generation mode, biomedical research tool 10 then identifies statistically significant correlates of these groups, and assigns clinical/experimental features to each.

Once a hypothesis has been generated, biomedical research tool 10 identifies samples against which the hypothesis can be tested. Certain inclusion and exclusion eligibility criteria can be considered and used to filter the content of the database to identify subjects/samples/experiments with certain characteristics. Biomedical research tool 10 also allows samples to be selected based upon the extent of any attribute(s). For example, the investigator may be primarily interested in only a subset of the sample population that displayed the greatest and least extensive toxicity to a given drug. This is assisted through the selection of the trait of interest and setting the extent of the trait (i.e., by defining standard deviations from the population mean). This feature may be particularly important in retrospective analysis of large clinical trial cohorts, since the outliers for a given trait can be identified prior to sample procurement.

Once the sample population is selected, the hypothesis is tested across the series of selected samples in a 2-step process. A subset of the samples (typically defined as a training set) are selected (either logically or at random) from each subgroup (for example disease versus control) to develop a discrimination algorithm that identifies statistical correlates of the feature in question. It is worthwhile to note that biomedical research tool 10 identifies clinical, experimental, and molecular correlates of the selected feature(s), thereby integrating both clinical and molecular data into the potential diagnostic algorithm. The user can exclude any attribute from the input to the training algorithm. In a second cross-validation test, the trained algorithm is applied to the remainder of the samples (in retrospective mode of operation, with known outcome), to determine if the test could have accurately predicted the nature of the remaining samples.

In this example, a hypothesis generated from analysis of unsupervised clustering of gene expression data includes the prediction of survival time of patients based upon the underlying genomic signatures of a tumor or other medical condition. Thus, patients with the shortest and longest survival time following surgery were placed into two groups. Each group was then randomly divided into two additional groups, the training set and the test set. The discriminating clinical and molecular features are first identified using a standard t-statistic for numerical data and chi squared for binary and text data. This test statistic is then used in a weighted voting metric. Data are first converted to a respective z-score in order to normalize data of different types to a similar scale where the z-score is the number of standard deviations from the mean. A more refined statistical package, which will more rigorously integrate the binary and non-binary data, is currently in the process of being implemented into the biomedical research tool 10 solution. In this fashion, the experimental, molecular, and clinical attributes that statistically correlate with survival time are first identified.

Experimental variables (i.e., those which may denote a variation in experimental protocol or quality) can also be identified that correlate with patient survival time. The clinical parameters platelet count and T-stage and can be included into the training algorithm. In addition, genes may also be identified, the expression of which correlates with survival time ($p<0.05$). Each attribute (platelet count, stage, and individual genes) can then be weighted based upon the calculated t-statistic within the training group. A discrimination score (the sum of the t-statistic multiplied by the normalized z-score for each attribute) can then calculated for each sample within the training groups and a threshold decision point is set halfway between the means of test groups. Alternatively, a user can set the threshold in order to maximize either sensitivity or specificity of the assay, or set it to a value which would demarcate an acceptable test failure rate. In this fashion, the end-user can set the decision point of the classification algorithm on the side of false positives or false negatives based upon the clinical consequence of the test result.

For example, if a positive test results in administration of a poorly tolerated treatment, the physician would typically error on the side of false negatives. At this time, a discrimination score is calculated for the remaining test samples, compared to the threshold decision point, and assigned a classification. The predicted classification is then compared to the actual outcome. While complicated, biomedical research tool 10 performs this cross-validation metric in a matter of seconds. Once validated, the classification algorithm is stored within biomedical research tool 10, such that it can be applied to any future sample. Thus, through the capture of standardized clinical, experimental, and molecular data, hypotheses can be rapidly generated and tested, and further developed into potentially useful diagnostic applications.

This information is then used with an algorithm which starts with a set of experimentally identified network nodes. These, for example, could be derived from a set of differentially expressed genes identified by a microarray or from a set of up- or down-regulated proteins identified by mass-spectrometry. Thereafter, sets of genes or proteins are mapped onto the global database of protein-protein interactions. This database is a unique resource that typically contains over 200,000 protein-protein and protein-small molecule interactions manually extracted from the literature by a group of experts. To address the issue of network hubs providing most of the "shortest path" connectivity in biological networks the relative contribution of every node is accessed in a condition-specific network compared to its role in the global network as described herein. Thus, the hubs which do not have any special role related to the set of genes/proteins of interest will be penalized, even though they may be highly connected. On the other hand nodes that are truly relevant for providing connectivity among experimentally-derived genes or proteins would be highly scored regardless of the total number of interactions they have.

Figure 5:
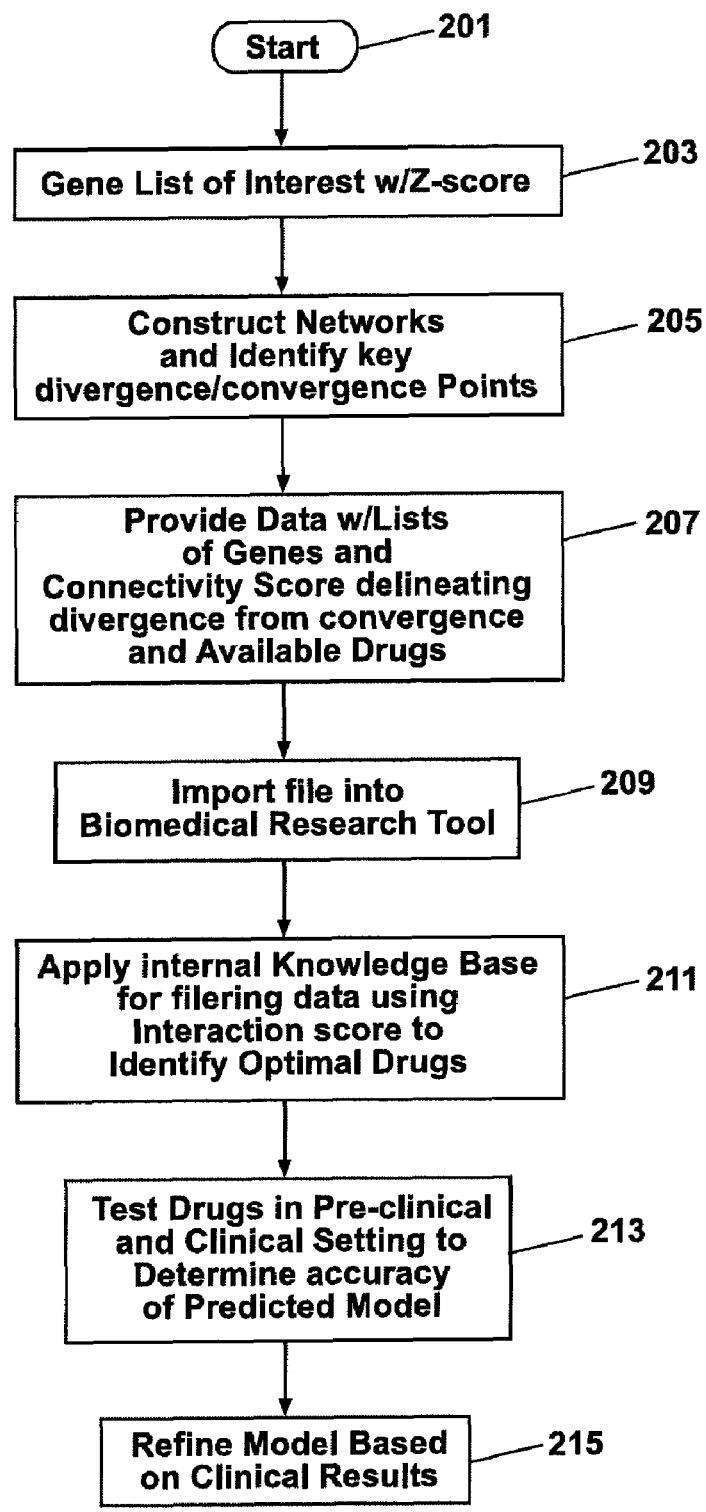
FIG. 5 is a flowchart diagram illustrating the use of functional annotation information is used with co-clustering algorithms to predict functionality of genes/proteins where scoring nodes are provided from in a set of experimentally-derived condition-specific genomic or proteomic profiles.

FIG. 5 illustrates the process 200 using a distribution for node prioritization and reconstructing significant pathway modules. The method begins 201 where a list of genes of interest with a corresponding z-score are provided to an algorithm 203. As described herein, networks are then constructed and used to identify key divergence/convergence points 205. Once determined, data with a list of genes and their connectivity score are provided so to delineate divergence from convergence such that available drugs are identified for those genes of interest 207. This data is imported back into the biomedical research tool and/or database 209 where an internal knowledge base is applied to this data where it is filtered and provided with an "interaction score" to identify optimal drugs 211. These drugs can then be tested in a pre-clinical and clinical setting to determine accuracy of the predicted model 213. Based on the outcome of these clinical results, the model can then be refined 215.

In order to provide a connectivity score based on the divergence and convergence points of the various genes with applicable drugs, an algorithm is used having a set of experimentally identified network nodes. In operation, it is assumed that K is a set of experimentally-derived nodes of interest (e.g., nodes representing differentially expressed genes). K is the subset of the global network of size N. The first step is the construction of a directed shortest path network connecting nodes from K to one other. This shortest path network S is constructed by building, wherever possible, directed paths from each node in K to other nodes in K, traversing via other nodes in the global network. This network is a set of putative regulatory pathways by which nodes from K could influence each other. Because of the high degree of connectivity among proteins, resulting shortest path networks are usually large and contain many false positives—cascades that are never realized in a cell. The S is a subset of N and may contain nodes in addition to K. Some nodes from K may become "internal" in S—i.e., they are lying on the shortest paths while the rest are either "source" or "sink" terminals of the shortest paths. All nodes in S that are not in K are by definition "internal" nodes. It should recognized that S is referred to as a condition-specific shortest path network.

It will be recognized that building of this shortest path network is executed by a standard Dijkstra algorithm. Often there are multiple paths of the same length connecting two nodes and assembling the shortest paths may result in a substantially large network. By way of example, if the process were to start with 100 differentially expressed genes, the resulting network can contain 1,500-2,000 nodes. If node i ∈ S and one of the nodes of the experimental set j ∈ K were considered, in addition to condition-specific network S, the shortest path networks are calculated between j and every other node in the global network, wherever such shortest paths exist (up to N-1 pairs). This number is $N_j \leq N-1$. A determination is made as to how many of these contain node i. This number is in turn $N_{ij} p \leq N_j \leq N-1$. Similarly, it can also be determined how many times node i occurs in $K_j$ shortest paths networks connecting j to all other nodes in K. This number is $K_{ij} \leq K_j \leq K-1$.

It will be further recognized that node i is counted only once for every pair from K, even though it may be part of multiple linear shortest paths connecting the same pair. Under the "null" hypothesis that node i has no special role in connecting node j to the rest of differentially expressed genes in K, the probability to observe i in $K_{ij}$ or larger number of the shortest path networks originating at j follows hyper-geometric distribution. Indeed this problem can be recast as one of the selection without replacement. For a node j ∈ K the number of shortest paths to every other node of the global network is $N_j \leq N-1$ of which $N_{ij}$ are "marked" by the fact that they contain node i. On the other hand, a set of $K_j$ paths to the rest of K-1 experimentally derived nodes represents a "selection." If node i has no special role for connecting j to the rest of the nodes in K, then the number of "marked" shortest path networks in the selection should follow the hyper-geometric distribution. The probability that among the shortest path networks of node j $K_{ij}$ would contain node i is given by the p-value according to the equation:

$$p_{ij}(K_{ij}) = \frac{\binom{N_{ij}}{K_{ij}}\binom{N-N_{ij}-1}{K-K_{ij}-1}}{\binom{N-1}{K-1}} = \frac{N_{ij}!(K-1)!(N-N_{ij}-1)!(N-K)!}{K_{ij}!(N-1)!(N_{ij}-K_{ij})!(K-K_{ij}-1)!(N-N_{ij}-K+K_{ij})!}$$

If this procedure were repeated for all nodes in K, calculating up to K p-values for each node i in the network of shortest paths connecting differentially expressed genes called $p_i$. Each of these p-values shows relevance of node i to individual members of the set K. As the nodes are identified which are statistically significant to at least one or more members of the experimental set, the "topological significance" score associated with node i is defined as the minimum of the $p_{ij}$ values. Hence, the formula as described above is a distribution. The process as described herein is unique in that this distribution is used to describe statistics of the shortest path where the resulting probabilities are used for scoring nodes in the network. Consequently, the manner in which the parameters of the equation are defined in terms of network paths is also unique.

Hypothetical results in using this distribution have demonstrated that the method of the invention can prioritize nodes based on topological significance. Highly-scored nodes have a much better chance to be related to the disease compared to all other nodes in the shortest path network and compared to all differentially expressed nodes. Thus, it has been established that topologically significant network nodes identified by the invention are likely to be highly relevant to the disease phenotype. This opens new methods to predict and validate drug targets by using the concept of "drugable" network modules. These modules are small sub-networks which, when affected by drugs are likely to have significant impact on a disease. Identification of such modules starts with a set of genes or proteins differentially expressed in a set of disease samples. The aim is to predict which nodes are placed in key network positions to be likely regulators of disease-response genes and proteins. Thus, the distribution applied to a network node can be assigned multiple significance scores. Each score evaluates its role with respect to one of the differentially expressed genes. The score could be viewed as strength of "functional" connection between the node and that gene. Strong functional connection (low p-value) implies that the node plays a key role in providing connectivity between such gene and the rest of the differentially expressed set.

More specifically, the distribution may be described as a "topological significance" algorithm as it assigns scores to network nodes based on their importance in providing connectivity among the set of nodes derived from genes or proteins in a user's experiment ("experimental" nodes). To perform such scoring, the process begins by building shortest paths between each node in the global protein interaction network where the remainder of the nodes in this network which could be reached from the first node by directed network paths. Additionally, given a set of condition-specific "experimental" network nodes (for example, identified by mapping a set of differentially expressed genes) the shortest paths are built from every experimental node to the rest of experimental nodes, wherever such paths exist. Each node in such condition-specific shortest path network is scored based on comparing the number of shortest paths networks" in the experimental set which are passed via this node to a number of such paths in the global set which also take into account relative size of the experimental set with relation to the size of global network. Hence, if the number of shortest paths for the experimental set containing the node in question represent somewhat higher fraction of all shortest paths containing that node, then the experimental set is expressed as a fraction of the global network where the node in question is highly scored.

To best understand how this distribution works, it should be assumed that K is a set of experimentally-derived nodes of interest (e.g., nodes representing differentially expressed genes) where K is a subset of the global network of size N. The first step in this process in the construction of a directed shortest path network involves connecting nodes from K to one other. This shortest path network S is constructed by building, wherever possible, directed paths from each node in K to other nodes in K, traversing via other nodes in the global network. This network is a set of putative regulatory pathways by which nodes from K can influence each other. Because of the high degree of connectivity among proteins, resulting shortest path networks are usually large and contain many false positives, i.e., cascades that are never realized in a cell. The S is a subset of N and may contain nodes in addition to K. Some nodes from K may become "internal" in S—i.e., they are lying on the shortest paths while the rest are "source" or "sink" terminals of the shortest paths. All nodes in S that are not in K are by definition "internal" nodes. For future reference we call S a condition-specific shortest path network. Building of this shortest path network is executed by standard a Dijkstra algorithm that is known to those skilled in the art. Often there are multiple paths of the same length connecting two nodes—in this case all such paths become part of the shortest paths network. Put together, the shortest paths usually constitute a fairly large network. For example if one starts with 100 differentially expressed genes, the resulting network would typically contain 1,500-2,000 nodes.

Let's consider node $I \in S$ and one of the nodes of the experimental set $j \in K$. In addition to condition-specific network S, the shortest path networks are calculated between j and every other node in the global network, wherever such shortest paths exist (up to N-1 pairs). This number is $N_j \leq N-1$. Thereafter the number of paths containing contain node I are counted. This number is in turn $N_{ij} \leq N_j \leq N-1$. On the other hand we can count how many times node i occurs in $K_j$ shortest path networks connecting j to all other nodes in K. This number is $Kij \leq K_j \leq K-1$. Note that we count node i only once for every pair from K, even though it may be part of multiple linear shortest paths connecting the same pair. Under these conditions the probability that node i would be present $K_{ij}$ times or more in the shortest path networks of j by chance follows hypergeometric distribution. Indeed this problem can be recast as one of selection without replacement. For a node $j \in K$, the number of shortest paths to every other node of the global network is $N_j \leq N-1$ of which $N_{ij}$ are "marked" by the fact that they contain node i. On the other hand, $K_j$ paths to the rest of K-1 experimentally derived nodes represent a "selection." If node i has no special role for connecting j to the rest of nodes in K, then the number of "marked" shortest path networks in a selection should follow the hypergeometric distribution.

As shown on FIG. 6A, a node (X) is provided that can have either upstream or downstream significant connections to a differentially expressed gene (G). X is significant with respect to providing connectivity between G and other differential expressed genes. Functional links have directionality. On the leftmost network, the node X provides connectivity between differentially expressed gene G and its downstream targets, while on the network to its right, X connects G and multiple other differentially expressed genes upstream of it. Some nodes may have multiple "functional" links with good strength. These nodes may be referred to as "functional hubs." These functional hubs are quite different from "physical hubs" (network nodes with large numbers of physical interactions), in that "functional hubs" are condition specific—they only have a special role for connecting genes or proteins differentially expressed under certain conditions. Also, functional hubs do not have to have large numbers of physical interactions themselves. More likely they will be "bottleneck" nodes, providing unique "bridges" between parts of the global network. As seen in FIG. 6B, some functional hubs may have the majority of their links downstream while others would have them upstream. Node X may have more than one significant connection depending on the number of connections upstream, and downstream X can be called either a divergence hub or convergence hub. These "divergence" and "convergence" hubs may play fundamentally different roles in disease and drug response. Therefore, affecting them with drugs will have different consequences. Finally, as seen in FIG. 6C, more complex patterns of functional connectivity may also be considered, where a differentially expressed gene is connected to a multitude of its regulators or targets via multiple significant nodes. Differentially expressed genes may become function hubs themselves if they have many significant connections. Functional hubs may typically be considered priority drug targets since they have significant impact on the system. Moreover, the role of these nodes as functional hubs is specifically defined within the context of a disease, while they may have less importance under normal conditions. Thus, unlike affecting physical hubs, targeting the functional hubs with drugs is likely to maximize impact on the disease while minimizing effects on general physiological processes.

Functional analysis of the sets of genes linked to hubs by upstream and downstream functional connections provides further insight regarding their relevance to a specific disease. In using this analysis, corresponding genes may be mapped onto a standard Gene Ontology, as well as other process and disease ontologies currently available. This step allows selecting functional hubs that have the most significant impact on disease-related processes or disease-related genes. A final step is ranking functional hubs based on their "drugability." In this step the nodes can be screened against the database of targets for drugs currently on the market or molecules in the development pipeline. The end-point of this analysis of a disease gene expression profile is a set of network modules that originate from functional hubs that are prioritized based on their potential functional impact and compound availability. For each module the analysis also identifies affected biological processes and disease related genes. As seen in FIG. 5, this correlation between biological processes, disease-related genes, and applicable drugs is then imported back into a biomedical research tool or database. An internal knowledge base is subsequently applied to this data in order to filter and provide an "interaction score" for identifying optimal drugs for use in disease treatment. These drugs can then be tested in a pre-clinical and clinical setting to determine accuracy of the predicted model. Based on the outcome of these clinical results, the model can be continually refined.

Figure 7:
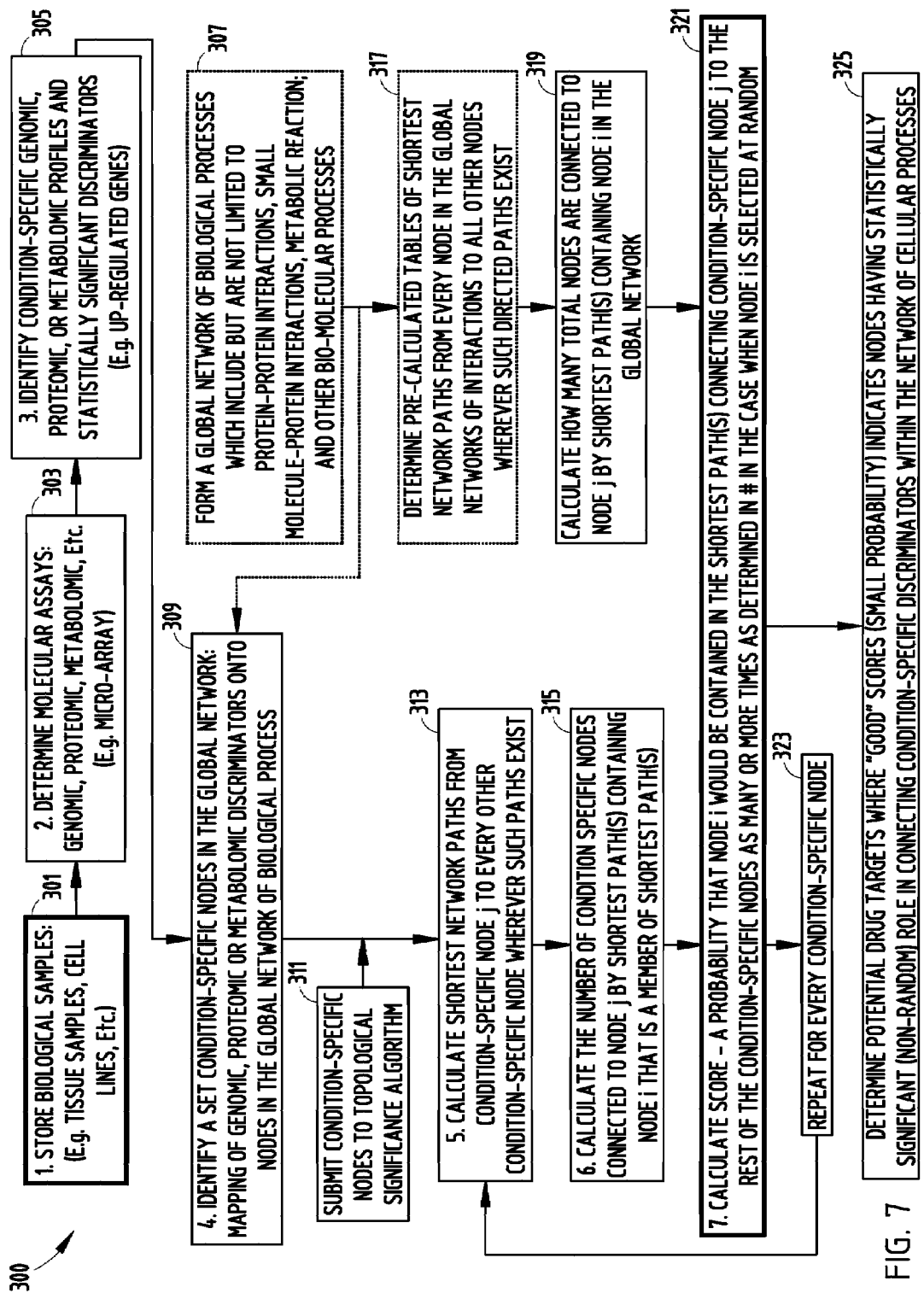
FIG. 7 is a flowchart diagram illustrating the process used to determine probability scoring.

Finally, FIG. 7 illustrates a flowchart diagram illustrating the process used to determine probability scoring. This scoring process begins with a plurality of biological samples 301, such as tissue samples, cell lines, or the like. These samples are combined to product molecular assays 303 including, but not limited to, genomic, proteomic, metabolic, etc. Condition profiles are then identified 305 and statistically significant discriminators are determined. A global network of biological processes are collected and stored 307 which are supplied to the metabolic profiles in order to identify a set condition specific nodes in the global network of biological processes 309. As noted herein, the condition specific nodes are submitted to a topological significant algorithm 311 such that the shortest network path from a condition specific node to every other condition specific node is calculated where such paths exist 313. For example, from a node (j), the shortest network path would be calculated from node (j) to every other condition specific node. Thereafter, for a second node (i) that is a member of the shortest calculated network paths, those condition specific nodes are counted for each node connect to node (j) by shortest path conditioning the second node (i) 315.

From the collection of global biological processes 307, tables are precalculated of shortest network paths from every node in the global network of interactions to all other nodes wherever such direct paths exist 317. The total number of nodes that are connected by the first node by the shortest path(s) containing the second node in the global network is counted 319. Using the total number of nodes 319 and the number of condition specific nodes 315, a score is calculated 321. The score is based upon the probability that node (i) would be contained in the shortest path connecting condition specific node (j) to the rest of the condition specific node j to the rest of the condition specific nodes as many or more times as determined in step 315 in the case when node (j) is selected at random. As noted herein, the probability is calculated using hypergeometric distribution with parameters determined by the number of nodes in the global network and the number and condition specific nodes. This process is repeated such that a new score is calculated for every condition specific node 323. Thereafter, good scores (small probability) indicate nodes having statistically significant (non-random) role in connecting condition specific discriminators within the network of cellular processes 325.

Thus, the system and method of the present invention allows for the analysis of stored data received from a variety of experimental platforms, as well as association with pre-clinical and clinical sources. The biomedical research tool and its associated systems and methods described herein is a fully integrated medical informatics/molecular bioinformatics database/analysis package that can be used in areas such as accelerated target discovery, diagnosis, and treatments for molecular-based diseases. A key feature of the present invention is its two-way directionality that allows for detailed genotype to phenotype analysis and application of specific drug treatments for these genes. According to the invention, molecular-based classification of samples from various subjects within the database initially identifies the discrete stratifications of subjects/samples at the molecular level; biomedical research tool then identifies subject, sample and experimental parameters that statistically correlate with this molecular-based classification (so called "hypothesis generator"). Since biomedical research tool represents both a database for tracking subjects and samples along with extensive medical informatics, as well as the necessary statistical analysis tools, the developed hypothesis can be readily tested on additional samples within the database. If validated, biomedical research tool develops the optimal diagnostic test, identifies genes/proteins that may represent biomarkers of the particular feature in question (disease, response to treatment, etc.), and identifies known drug targets with corresponding drugs and possible novel targets for future therapeutic intervention.

The invention represents a complete medical/molecular informatics solution where subjects (patients, animal models, cell lines) are added to the database together with all the collected information. This can be performed manually, or through auto-extraction routines from selected standardized informatics databases. Coupled with detailed functional annotation, co-clustering algorithms can be used to predict functionality of novel genes/proteins where a computational algorithm allows scoring nodes in a network built from a set of experimentally-derived, condition-specific genomic or proteomic profiles. The scoring is based on the relative role the nodes are playing in providing connectivity among genes or proteins of interest compared to their role in the global network. The method is, therefore, neutral with respect to the node's degree or centrality. Hubs that are important for a condition represented by the molecular profile will be scored high, while those that appear on the network by chance will be downgraded. Moreover, the output of this distribution is a set of prioritized network nodes along with their possible regulatory effects on other genes and proteins. Such output gives researchers a set of hypotheses that can be tested by affecting or measuring changes in activity of individual high ranking proteins while observing the effects of such changes on the phenotype of interest.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed:

1. A method for determining genotype analysis for an application of specific drug treatments for identified genes using at least one database comprising the steps of:

identifying at least one condition-specific genomic, proteomic or metabolic profile;

identifying a statistically significant discriminator;

accessing a global network defining known biological molecular processes;

identifying a set of condition-specific nodes in the global network;

calculating at least one shortest network path from a first node (j) to every other condition-specific node wherever a path exists in the global network;

counting the number of condition specific nodes connected to the first node (j) by the shortest path containing a second node (i);

determining a pre-calculated table of the shortest network paths from every node in the global network of interactions to all other nodes wherever such directed paths exist;

counting the total number of nodes that are connected to the first node (j) by a shortest paths containing the second node (i) in the global network;

calculating a probability score using a hypergeometric distribution with parameters determined by the number of nodes in the global network and number of condition specific nodes and number of nodes connected to the first node (j) by the shortest network paths containing the second node (i);

utilizing the probability score for providing connectivity among genes or proteins of interest to assess role of nodes in the application of specific drug treatments; and wherein the hypergeometric distribution is $$p_{ij}(K_{ij}) = \frac{\binom{N_{ij}}{K_{ij}}\binom{N-N_{ij}-1}{K-K_{ij}-1}}{\binom{N-1}{K-1}} =$$

$$\frac{N_{ij}!(K-1)!(N-N_{ij}-1)!(N-K)!}{K_{ij}!(N-1)!(N_{ij}-K_{ij})!(K-K_{ij}-1)!(N-N_{ij}-K+K_{ij})!}$$

such that $P_jK_{ij}$ is the probability of determining the shortest path network of nodes i and j; K is a set of experimentally-derived nodes of interest; and N is the total number of network nodes; and outputting a result to a user of the applicable drugs with the genomic or proteomic profiles, wherein all steps are performed on a processor.

2. A method for determining genotype analysis as in claim 1, wherein a small probability score indicates nodes having statistically significant role in connecting condition specific discriminators within the network of cellular processes.

3. A system for performing biomedical research comprising:

a first database for classifying molecular-based samples from various subjects;

a second database utilizing a plurality of predetermined tables of shortest network paths for a network of identified biological processes; and a processor for determining at least one statistically-significant discriminator using a computational distribution for scoring nodes in a network built from a set of experimentally-derived condition-specific genomic or proteomic profiles to identify applicable drugs with the genomic or proteomic profiles using the computational distribution $$p_{ij}(K_{ij}) = \frac{\binom{N_{ij}}{K_{ij}}\binom{N-N_{ij}-1}{K-K_{ij}-1}}{\binom{N-1}{K-1}} =$$

$$\frac{N_{ij}!(K-1)!(N-N_{ij}-1)!(N-K)!}{K_{ij}!(N-1)!(N_{ij}-K_{ij})!(K-K_{ij}-1)!(N-N_{ij}-K+K_{ij})!}$$

such that $P_jK_{ij}$ is the probability of determining the shortest path network of nodes i and j; K is a set of experimentally-derived nodes of interest; and N is the total number of network nodes; and wherein a result is displayed to a user of the applicable drugs with the genomic or proteomic profiles.

4. A system for performing biomedical research as in claim 3, wherein the scoring is based on the relative role of a node in providing connectivity among genes or proteins of interest compared to their role in the network.

5. A system for performing biomedical research as in claim 3, wherein a small probability score indicates nodes having statistically significant role in connecting condition specific discriminators within the network of cellular processes.

* * * * *

UNITED STATES PATENT AND TRADEMARK OFFICE
CERTIFICATE OF CORRECTION

| | | |
|---|---|---|
| PATENT NO. | : 7,660,709 B2 | |
| APPLICATION NO. | : 11/945692 | |
| DATED | : February 9, 2010 | |
| INVENTOR(S) | : Andrej Bugrim et al. | |

It is certified that error appears in the above-identified patent and that said Letters Patent is hereby corrected as shown below:

Column 1
Line 27, after "performing" delete "a".
Line 35, after "suitable" insert -- for --.

Column 2
Line 30, "or" should be -- of --.
Line 41, after "cases" insert -- , --.
Line 44, "are" should be -- is --.
Line 48, "were" should be -- where --.
Line 51, after "approach" delete ",".

Column 3
Line 14, after "allowing" insert -- one --.
Line 34, "is" should be -- as --.
Line 36, after "from" delete "in".
Line 56, "system" should be -- systems --.

Column 4
Line 7, "proceeded" should be -- preceded --.
Line 29, "a" should be -- and --.

Column 5
Line 6, "cell" should be -- cells --.
Lines 23 and 25, delete "from".

Column 7
Line 31, "1216" should be -- 12-16 --.

Signed and Sealed this
Twenty-fourth Day of May, 2011

David J. Kappos
*Director of the United States Patent and Trademark Office*

Column 8
Line 35, "principle" should be -- principal --.
Line 41, "though" should be -- through --.
Line 47, "FIG. 2-1" should be -- FIG. 1 --.

Column 9
Line 30, "on" should be -- of --.

Column 10
Line 40, "tells" should be -- tell --.
Line 44, "users" should be -- user's --.

Column 11
Line 18, "correlate" should be -- correlates --.
Line 22, "correlate" should be -- correlates --.

Column 12
Lines 5 and 6, "hypothesis" should be -- hypotheses --.
Line 11, "stem" should be -- stems --.
Line 12, "hypothesis" should be -- hypotheses --.
Line 12, after "best," delete "since".
Line 45, "introduces" should be -- introduced --.
Line 49, "discriminate" should be -- discriminates --.

Column 13
Line 57, "are" should be -- is --.

Column 14
Line 33, after "then" insert -- be --.

Column 15
Line 48, after "should" insert -- be --.
Lines 62, 64 and 67, "$\leqq$" should be -- $\leq$ --.
Line 64, "$N_{ij}p \leqq N_j \leqq N\text{-}l$" should be -- $N_{ij} \bullet N_j \bullet N\text{-}l$ --.

Column 16
Line 11, "$\leqq$" should be -- $\leq$ --.

Column 17
Line 11, after "network" delete "which".
Line 16, after "of" insert -- the --.
Line 18, "networks" in" should be -- networks in --.
Line 49, "standard a Dijkstra" should be -- standard Dijkstra --.

Lines 60, 62 and 65, "≦" should be -- ≤ --.
Line 61, "containing contain node I" should be -- containing node i --.
Line 65, "Kij≦K$_j$≦K-l" should be -- Kij • K$_j$ • K-l --.

Column 18

Line 6, "≦" should be -- ≤ --.
Lines 16 and 17, "differential" should be -- differentially --.
Line 45, "function" should be -- functional --.

Column 19
Line 4, "disease related" should be -- disease-related --.
Line 19, "product" should be -- produce --.
Line 24, "identify a set" should be -- identify set --.
Line 27, "topological" should be -- topologically --.
Line 34, "connect" should be -- connected --.
Line 55, "role" should be -- roles --.

Column 20
Line 39, "effects" should be -- affects --.
Lines 41 and 42, "affecting or measuring ... the effects" should be -- effecting or measuring ... the affects --.
Line 52, after "of" insert -- the --.
Line 55, after "as" delete "a".

Column 21
Claim 1, Line 16, "paths" should be -- path --.
Claim 1, Line 25, "role" should be -- roles --.
Claim 1, Line 39, "P$_j$K$_{ij}$" should be -- p$_j$K$_{ij}$ --.

Column 22
Claim 2, Line 3, "role" should be -- roles --.
Claim 3, Line 30, "P$_j$K$_{ij}$" should be -- p$_j$K$_{ij}$ --.
Claim 5, Line 42, after "having" insert -- a --.